(12) United States Patent
Kurihara et al.

(10) Patent No.: US 7,845,231 B2
(45) Date of Patent: Dec. 7, 2010

(54) SHEAR MEASURING METHOD AND ITS DEVICE

(75) Inventors: Kazue Kurihara, Sendai (JP); Hiroshi Sakuma, Sendai (JP); Masashi Mizukami, Sendai (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 438 days.

(21) Appl. No.: 12/088,046

(22) PCT Filed: Sep. 27, 2006

(86) PCT No.: PCT/JP2006/319103

§ 371 (c)(1),
(2), (4) Date: Mar. 25, 2008

(87) PCT Pub. No.: WO2007/037241

PCT Pub. Date: Apr. 5, 2007

(65) Prior Publication Data

US 2009/0145231 A1  Jun. 11, 2009

(30) Foreign Application Priority Data

Sep. 28, 2005 (JP) .............................. 2005-282768
Sep. 28, 2005 (JP) .............................. 2005-282769

(51) Int. Cl.
*G01H 13/00* (2006.01)
*G01N 3/24* (2006.01)
(52) U.S. Cl. .............................. 73/579; 73/659; 73/841
(58) Field of Classification Search .................. 73/579, 73/54.37, 659, 841
See application file for complete search history.

(56) References Cited

U.S. PATENT DOCUMENTS 4,173,142 A  11/1979  Heinz
(Continued)

FOREIGN PATENT DOCUMENTS

JP  61 132840  6/1986
(Continued)

OTHER PUBLICATIONS

Mizukami, Masashi et al., "Nono Kyoshin Zuri Sokuteiho Ni Yoru Nano Usumaku No Masatsu Nendansei Hyoka", DAI 56 KAI Divisional Meeting on Colloid and Interface Chemistry Koen Yoshishu, p. 235 (2003).

*Primary Examiner*—J M Saint Surin
(74) *Attorney, Agent, or Firm*—Oblon, Spivak, McClelland, Maier & Neustadt, L.L.P.

(57) ABSTRACT

A resonance shear measuring method capable of simple and rapid measurement by obtaining a resonance shear curve through Fourier transformation of a damping curve of an oscillation on one side surface of a sample during measurement of shear response from the sample is provided. The method is to measure shear response of the sample sandwiched between the solid surfaces of a resonance shear measurement unit along with a change in film thickness by applying an input signal $U_{in}$ to a horizontal driving section of the shear resonance measurement unit, by detecting an oscillation on one side surface of the sample sandwiched between solid surfaces of the resonance shear measurement unit as an output signal $U_{out}$ by means of a displacement gauge, and by applying the output signal $U_{out}$ along with the input signal $U_{in}$ to a resonance shear signal analyzer, wherein a damping curve of the oscillation on one side surface of the sample is Fourier transformed by a Fourier transformation section (5B) to obtain a resonance shear curve. Also provided is a twin-path type apparatus for shear stress measurement capable of precise measurement of shear stress by using a twin-path method by which a distance between opaque substrates can be measured.

17 Claims, 6 Drawing Sheets

U.S. PATENT DOCUMENTS

| | | | |
|---|---|---|---|
| 5,052,228 A * | 10/1991 | Haritonidis | 73/705 |
| 6,644,101 B2 * | 11/2003 | Hajduk et al. | 73/54.37 |
| 6,655,194 B2 * | 12/2003 | Hajduk et al. | 73/54.37 |
| 6,668,622 B2 * | 12/2003 | Hajduk et al. | 73/54.37 |
| 6,681,618 B2 * | 1/2004 | Hajduk et al. | 73/54.37 |
| 7,047,794 B2 * | 5/2006 | Hajduk et al. | 73/54.37 |
| 7,418,876 B2 * | 9/2008 | Armstrong et al. | 73/841 |
| 7,451,666 B2 * | 11/2008 | Johanson | 73/866 |
| 2008/0022758 A1 * | 1/2008 | Cottais et al. | 73/54.32 |
| 2010/0139375 A1 * | 6/2010 | Johns et al. | 73/54.24 |

FOREIGN PATENT DOCUMENTS

| | | |
|---|---|---|
| JP | 63 47602 | 2/1988 |
| JP | 63 135808 | 6/1988 |
| JP | 6 117824 | 4/1994 |

* cited by examiner

6CB

SHEAR MEASURING METHOD AND ITS DEVICE

TECHNICAL FIELD

The present invention relates a shear measurement method and an apparatus thereof which is capable of performing a desired measurement on an interface between two solid surfaces or a thin film sandwiched inbetween irrespective of their transparency, and more particularly and specifically relates to (1) a method and an apparatus for resonance shear measurement which is rapid, simple, convenient, versatile and precise in performing a measurement on a film with thickness which is liable to change or a highly volatile liquid film, and (2) a method and an apparatus to measure shear stress between two solid surfaces and a layer sandwiched inbetween including a liquid thin film, a liquid crystal thin film, or a polymer adsorption layer while changing the distance of the two solid surfaces in nanometer scale by using a measuring technique for the separation distance between the two surfaces by means of a twin-path type interferometer method.

BACKGROUND ART (1) First of all, it is important for comprehension and control of the friction and lubrication on solid surfaces and orientation and structuration of liquid molecules and liquid crystal molecules to know a shear response of a sample (such as liquid and liquid crystal) sandwiched between the solid surfaces along with change of film thickness in nanometer scale. The resonance shear measurement for measuring the shear response of a sample is a method to provide a shear by oscillating a surface on one side of a sample horizontally and to monitor its response near a resonance frequency. Plotting the shear response as a function of frequency gives a resonance curve. Resonance frequency and a resonance peak height are sensitive to the properties of the sample between the solid surfaces and immune to an oscillation noise from outside of the measurement apparatus.

The conventional method to measure precisely the shear response of a sample sandwiched between solid surfaces is to measure the shear response of the sample to a shear while changing frequency around the resonance frequency and to plot the response as a function of frequency to obtain a resonance shear curve. This method is disclosed in Non-Patent Document 1 shown below.

An apparatus for precise measurement of shear stress was proposed by the present inventors as described in Patent Document 1 below.

(2) Secondly, the present inventors have proposed an apparatus for precise measurement of shear stress capable of measuring with high accuracy a rheological behavior in an ultra small space with a nano-scale dimension, as described in Patent Document 2.

The present inventors have also proposed a surface force measurement apparatus and method capable of measuring a surface force between samples with high accuracy even if the samples are not transparent for light, as described in Patent Document 3 below.

[Patent Document 1] Japanese Patent Publication No. 3032152

[Patent Document 2] Japanese Patent Publication No. 3032152

[Patent Document 3] Japanese Patent Application Publication No. 2001-108603

[Non-Patent Document 1] Liquid Crystal, vol. 6, No. 1, pp. 34-41, 2002.

DISCLOSURE OF INVENTION

However, since shear response of a sample is measured at around the resonance frequency while changing the oscillation frequency, the conventional technique described above in (1) requires to keep the film thickness of the sample constant for a long time. It is therefore difficult to measure samples such as films with the thickness liable to change and liquid thin films with high volatility.

Furthermore, in the conventional technique described above in (2), an apparatus for resonance shear measurement is combined with a measurement apparatus for a distance between surfaces by an optical interferometry technique making use of the fringes of equal chromatic order (FECO) to measure rheological properties and friction/lubrication properties of a sample sandwiched by the surfaces while measuring the distance between the surfaces with resolution of 0.1 nanometer. Since this technique makes use of a light passing through the surfaces, the substrate and the sample sandwiched between the substrate surfaces are limited to be optically transparent. Especially, the substrate is almost limited to mica for a practical use, and an alternative substrate for an experimental test is also limited to a thin plate of sapphire and glass with thickness of about 2 micrometer.

In addition, the twin-path type surface forces apparatus as described in Patent Document 3 measures a force exerted to upper and lower surfaces and cannot perform a shear measurement.

The purpose of the present invention is to provide a shear measurement method and an apparatus thereof which can perform a desirable measurement not only on a transparent sample but also on an opaque sample.

More concrete description is given in the following.

By taking the situation described above into account, the first purpose of the present invention is to provide a method for resonance shear measurement, the method being capable of performing simple and short-time measurement by obtaining a resonance shear curve by Fourier-transforming a damping curve of an oscillation on a surface on one side of a sample during a measurement of a shear response from the sample.

In addition, by taking account of the situation described above, the second purpose of the present invention is to provide a twin-path type measurement method of shear stress and an apparatus thereof which enables a precise measurement of shear stress by making use of a twin-path method which is capable of measuring a distance between the substrates even when the substrates or a sample are not transparent.

To achieve the purpose describe above, the present invention provides:

[1] a resonance shear measuring method to measure a shear response of a sample sandwiched between solid surfaces in a resonance shear measurement unit, along with a change in film thickness, the method including steps of:

applying an input signal $U_{in}$ to a horizontal driving section of the resonance shear measurement unit, detecting an oscillation of a surface on one side of the sample sandwiched between the solid surfaces set in the resonance shear measurement unit by means of a displacement gauge, the output of detection being an output signal $U_{out}$, and, applying the output signal $U_{out}$ along with the input signal $U_{in}$ to a resonance shear signal analyzer, wherein a resonance shear curve is obtained by performing a Fourier transformation of a damping curve of the oscillation of the surface on one side of the sample.

[2] a resonance shear measuring method to measure a shear response of a sample which is solid surfaces themselves without any other sample sandwiched between the solid surfaces in a resonance shear measurement unit, along with a change in film thickness, the method including steps of:

applying an input signal $U_{in}$ to a horizontal driving section of the resonance shear measurement unit, detecting an oscillation of a surface on one side of the sample in the resonance shear measurement unit by means of a displacement gauge, the output of detection being an output signal $U_{out}$, and, applying the output signal $U_{out}$ along with the input signal $U_{in}$ to a resonance shear signal analyzer, wherein a resonance shear curve is obtained by performing a Fourier transformation of a damping curve of the oscillation of the surface on one side of the sample.

[3] the resonance shear measuring method according to item [1], wherein the sample is a thin film.

[4] the resonance shear measuring method according to item [1], wherein the sample is liquid.

[5] the resonance shear measuring method according to item [1] wherein the sample is a liquid crystal.

[6] the resonance shear measuring method according to item [1] wherein the sample has a thickness in nanometer size.

[7] the resonance shear measuring method according to item [1] or [2], wherein the sample has a surface modified by an adsorption or a chemical modification method.

[8] the resonance shear measuring method according to item [1] or [2], wherein the resonance shear curve is a frequency characteristics of shear response of the sample.

[9] an apparatus for resonance shear measurement including:

a waveform generator;

a power source to which the waveform generator is connected;

a resonance shear measurement unit to which the power source is connected and an input signal $U_{in}$ is applied;

a displacement gauge to which the resonance shear measurement unit is connected;

a resonance shear signal analyzer to which the displacement gauge and the power source are connected and to which an output signal $U_{out}$ along with an input signal $U_{in}$ are applied, the resonance shear signal analyzer including:

(a) a timer section, (b) a Fourier transformation section to which the timer section and the displacement gauge are connected, (c) an amplitude spectrum generation section to which the Fourier transformation section is connected, (d) a normalization section of amplitude ($U_{out}/U_{in}$), (e) a resonance shear curve producing section; and a computer to which the waveform generator and the resonance shear signal analyzer are connected.

[10] a twin-path type shear stress measurement method, wherein a shear stress measurement of a sample is performed by a combination of two methods: one method being a twin-path type measurement method for a distance between surfaces of the sample by irradiating a laser light to a mirror attached to a back side of a bottom disk holder and by detecting a phase change of the reflected light from the mirror, and the other method being the measurement method to measure rheological properties and friction/lubrication properties of the sample from a resonance curve.

[11] a twin-path type apparatus for shear stress measurement including:

(a) a precise shear device to give a horizontal displacement to a top disk holder, (b) a displacement gauge to detect the horizontal displacement of the top disk holder, (c) a fixing unit for fixing a lower surface of the sample, the unit comprising a leaf spring which holds at the front end a bottom disk holder, and a mirror disposed on a back side of the bottom disk holder, (d) a driving apparatus to drive upward and downward the bottom disk holder by driving the fixing unit for fixing the bottom disk holder, (e) a twin-path type measurement unit for measuring a distance between surfaces, the unit irradiating a laser light to the mirror and measuring a distance between the upper surface of the sample and the lower surface of the sample based on a phase change of a reflected light from the mirror, wherein rheological properties and friction/lubrication properties of the sample are measured per distance between the upper surface of the sample and the lower surface of the sample.

[12] the twin-path type apparatus for shear stress measurement according to item [11], wherein measurement on the rheological properties and friction/lubrication properties of the sample is performed based on a resonance curve of the sample.

[13] the twin-path type apparatus for shear stress measurement according to item [11] or [12], wherein the sample is a transparent sample or an opaque sample.

[14] the twin-path type apparatus for shear stress measurement according to item [11] or [12], wherein the sample is a liquid thin film.

[15] the twin-path type apparatus for shear stress measurement according to item [11] or [12], wherein the sample is a liquid crystal thin film.

[16] the twin-path type apparatus for shear stress measurement according to item [11] or [12], wherein the sample is an adsorption layer such as polymer and/or surfactant or a chemically modified film.

[17] the twin-path type apparatus for shear stress measurement according to item [11] or [12], wherein either one or both of the top disk holder and the bottom disk holder are opaque substrates.

DETAILED DESCRIPTION OF EMBODIMENTS OF THE INVENTION

A first embodiment of the present invention provides a resonance shear measuring method which measures a shear response of a sample sandwiched between solid surfaces in a resonance shear measurement unit, along with a change in film thickness, including steps of: applying an input signal $U_{in}$ to a piezoelectric element of the resonance shear measurement unit, detecting an oscillation of a surface on one side of the sample sandwiched between the solid surfaces set in the resonance shear measurement unit by means of a displacement gauge, the output of detection being an output signal $U_{out}$, and applying the output signal $U_{out}$ along with the input signal $U_{in}$ to a resonance shear signal analyzer. In the method, a resonance shear curve is obtained by performing a Fourier transformation of a damping curve of the oscillation of the surface on one side of the sample.

A second embodiment of the present invention provides a twin-path type apparatus for shear stress measurement which includes a precise shear device to give a horizontal displacement to an upper surface of a sample, a displacement gauge to detect the horizontal displacement of the upper surface of the sample, a fixing unit for fixing a lower surface of the sample which includes a leaf spring which holds at the front end the lower surface of the sample, and a mirror disposed on a back side of a bottom disk holder, a driving apparatus to drive upward and downward the lower surface of the sample by driving the fixing unit for fixing the lower surface of the sample, and a twin-path type measurement unit for measuring a distance between surfaces based on a phase change of a reflected light from the mirror. In the apparatus, rheological properties and friction/lubrication properties of the sample are measured per distance between the upper surface of the sample and the lower surface of the sample.

Embodiment

Various embodiments of the present invention will be described in more detail in the following.

Figure 1:
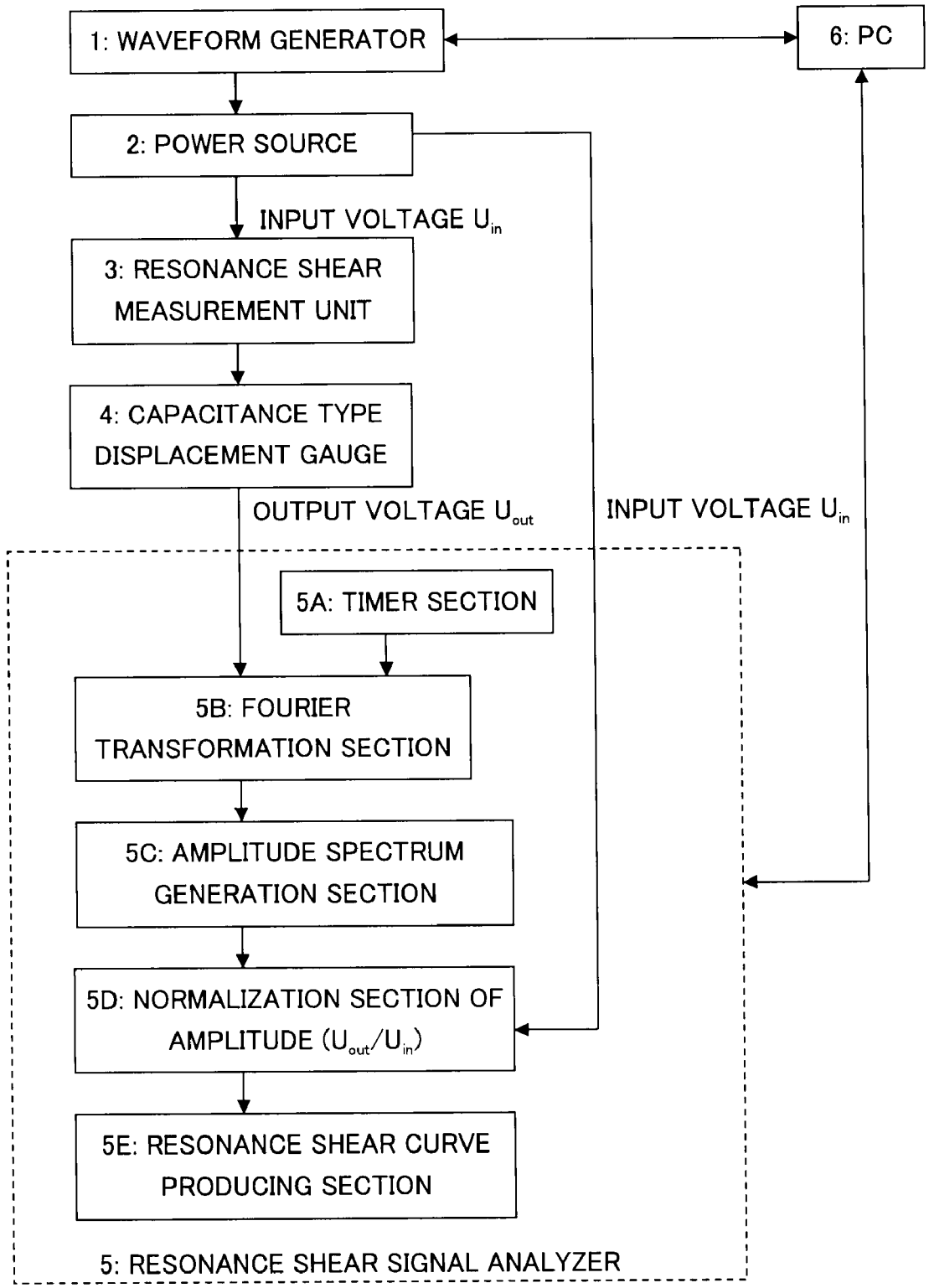
FIG. 1 is a schematic diagram of a resonance shear measurement system in accordance with an embodiment of the present invention.
Figure 2:
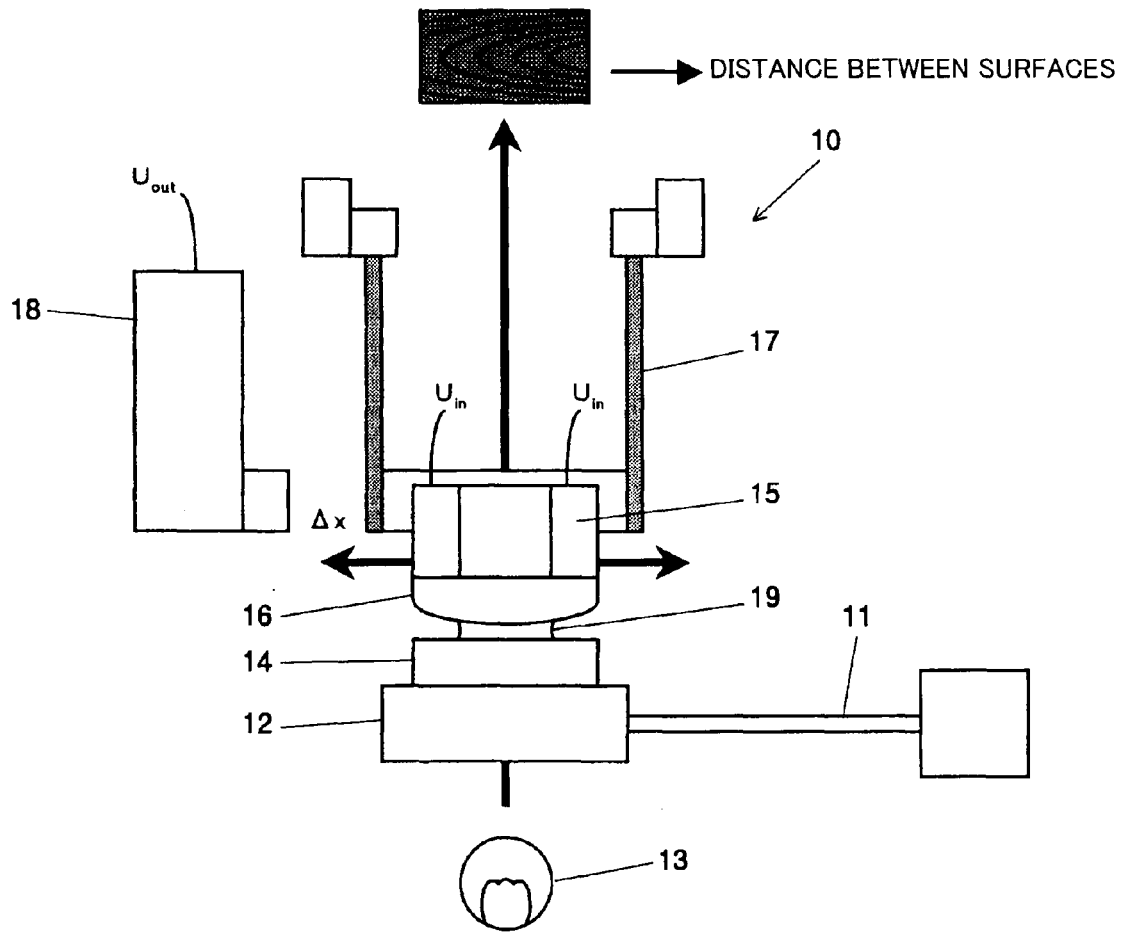
FIG. 2 is a schematic diagram showing an example of a resonance shear measurement unit of the resonance shear measurement system in accordance with an embodiment of the present invention.

FIG. 1 is a schematic diagram of a resonance shear measurement system in accordance with an embodiment of the present invention. FIG. 2 is a schematic diagram showing an example of a unit for resonance shear measurement of the system in accordance with an embodiment of the present invention. In these figures, reference numeral 1 is a waveform generator, 2 is a power source to which the waveform generator 1 is connected, 3 is a resonance shear measurement unit to which the power source 2 is connected and to which an input voltage $U_{in}$ as an input signal is applied, 4 is a displacement gauge such as, for example, a capacitance type displacement gauge, to which the resonance shear measurement unit is connected, 5 is a resonance shear signal analyzer to which the capacitance type displacement gauge 4 and the power source are connected and to which an output voltage $U_{out}$ as an output signal along with the input voltage $U_{in}$, are applied. The resonance shear signal analyzer 5 includes a timer section 5A, a Fourier transformation section 5B, an amplitude spectrum generation section 5C, a normalization section 5D of amplitude ($U_{out}/U_{in}$) to normalize $U_{in}(\omega)$ and $U_{out}$, and a resonance shear curve producing section 5E. 6 is a personal computer (PC) which is connected to the waveform generator 1 and the resonance shear signal analyzer 5.

In addition, the displacement gauge described above may be a strain gauge.

In FIG. 2, reference numeral 10 is a resonance shear measurement unit (corresponding to the unit 3 in FIG. 1), 11 is a cantilever, 12 is a disc holder, 13 is a white light source, 14 is a lower substrate fixed on the disc holder 12, 15 is a four-piece piezoelectric element as a horizontal driving section to drive horizontally the upper surface, 16 is an upper substrate fixed to the bottom of the four-piece piezoelectric element 15, 17 is a leaf spring to support the four-piece piezoelectric element 15, 18 is a capacitance type displacement gauge (a probe) to measure horizontal displacement $\Delta X$ of the leaf spring 17, (corresponding to a capacitance type displacement gauge 4 in FIG. 1), and 19 is a sample (solid, liquid, and liquid crystal and the like) which is an object for measurement of the shear response. The liquid may include not only a single component but also various liquid including micelle and colloid dispersion system with two or more components. Furthermore, a motor may be used as the horizontal driving section described above.

Figure 3:
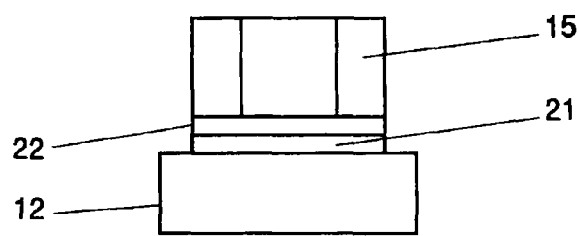
FIG. 3 is a schematic diagram of a partial configuration of a resonance shear measurement unit of the resonance shear measurement system in accordance with a modification of the present invention.

FIG. 3 is a schematic diagram of a partial configuration of a unit for resonance shear measurement of the resonance shear measurement system in accordance with a modification of the present invention.

In this example, substrates themselves are samples 21 and 22. Without any sample sandwiched between substrates as shown in FIG. 2, a friction (lubrication) property between the sample (substrate) 21 and the sample (substrate) 22 can also be measured.

Figure 4:
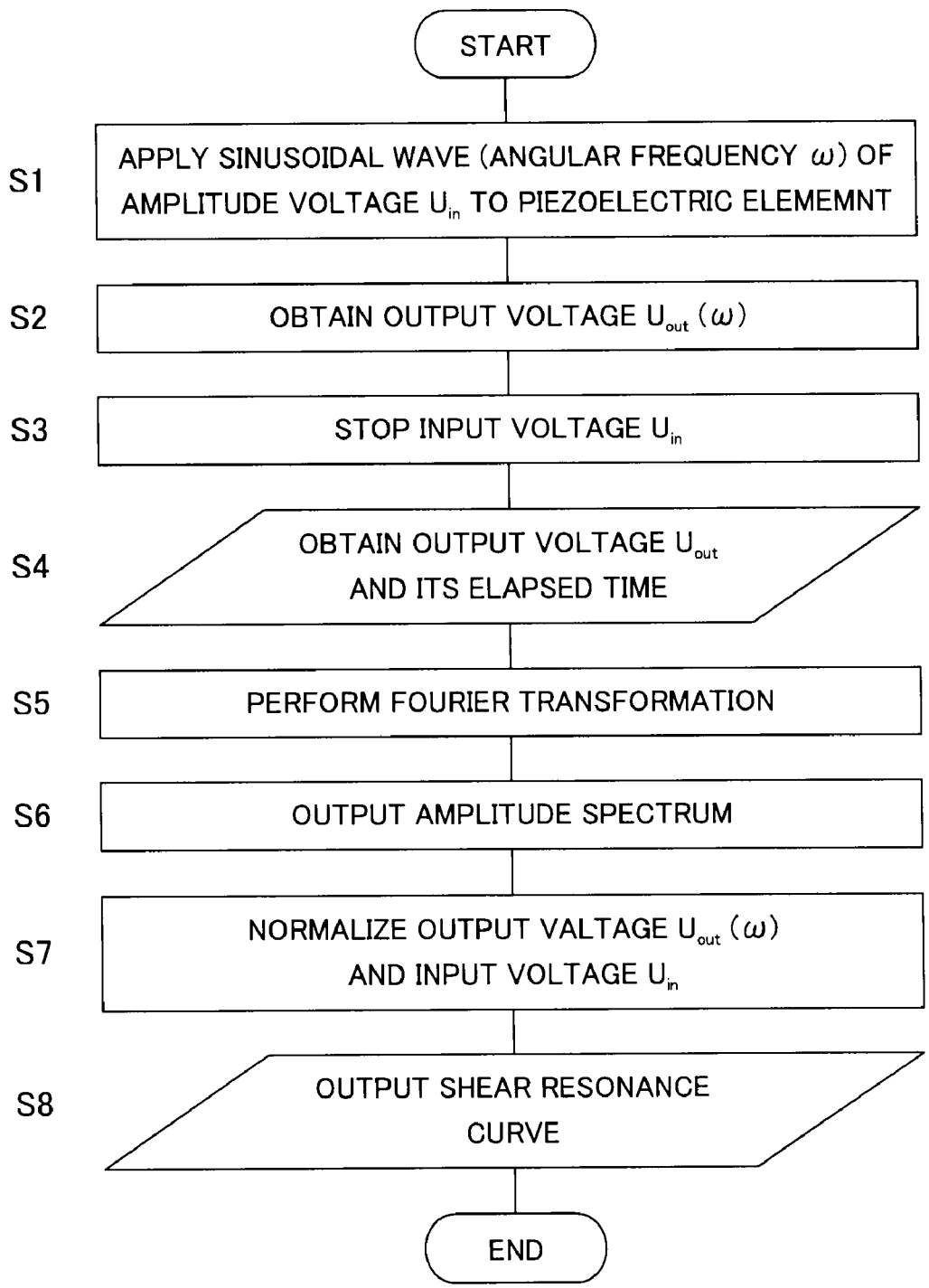
FIG. 4 is a flowchart of the resonance shear measurement in accordance with an embodiment of the present invention.

FIG. 4 is a flowchart of the resonance shear measurement.

(1) First of all, apply a sinusoidal wave (angular frequency $\omega$) of an amplitude voltage $U_{in}$ as shown in FIG. 1 to the piezoelectric element (the four-piece piezoelectric element 15 as shown in FIG. 2). (step S1).

(2) Obtain an output voltage $U_{out}(\omega)$. (step S2).

(3) Stop the input voltage $U_{in}$. (step S3).

(4) Obtain the output voltage $U_{out}$ along with its elapsed time. (step S4)

(5) Perform a Fourier transformation. (step S5).

(6) Output an amplitude spectrum. (step S6).

(7) Normalize the output voltage $U_{out}(\omega)$ and input voltage $U_{in}$. (step S7).

(8) Output a resonance shear curve. (step S8).

Figure 5:
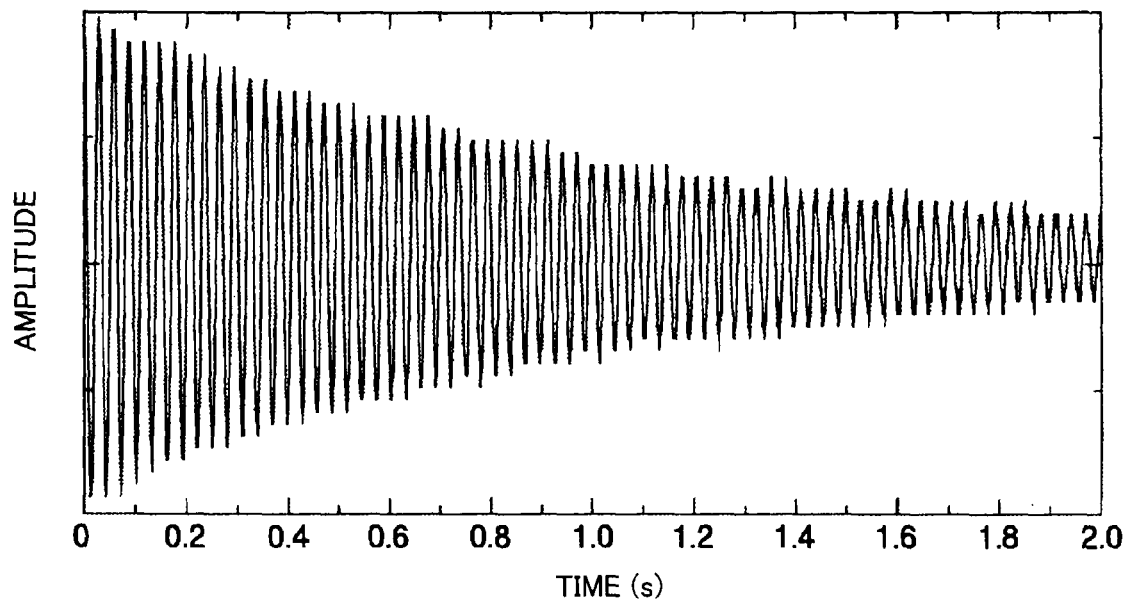
FIG. 5 shows an example of a damping oscillation of a surface on one side of a sample measured by setting the sample to the resonance shear measurement unit in accordance with the present invention.

When a measurement is performed for a sample set in the resonance shear measurement unit described above, the damping oscillation on the surface on one side of the sample exhibits a curve shown in FIG. 5.

Here the horizontal axis shows an elapsed time, and the vertical axis shows an amplitude of the oscillation. Fourier transformation expressed by the following Equation (1) is applied to the damping oscillation.

[Equation 1]

$$F(\omega) \int_{-\infty}^{+\infty} f(t)e^{-i\omega t} dt \quad (1)$$

By taking the amplitude spectrum, a resonance shear curve can be obtained. Here, ω is angular frequency, F(ω) is the obtained Fourier spectrum, f(t) is the damping oscillation, and t is time.

A measurement result of a resonance shear curve by using the resonance shear measurement method of the present invention is shown in the following in comparison with a result obtained by using the conventional method.

Figure 6:
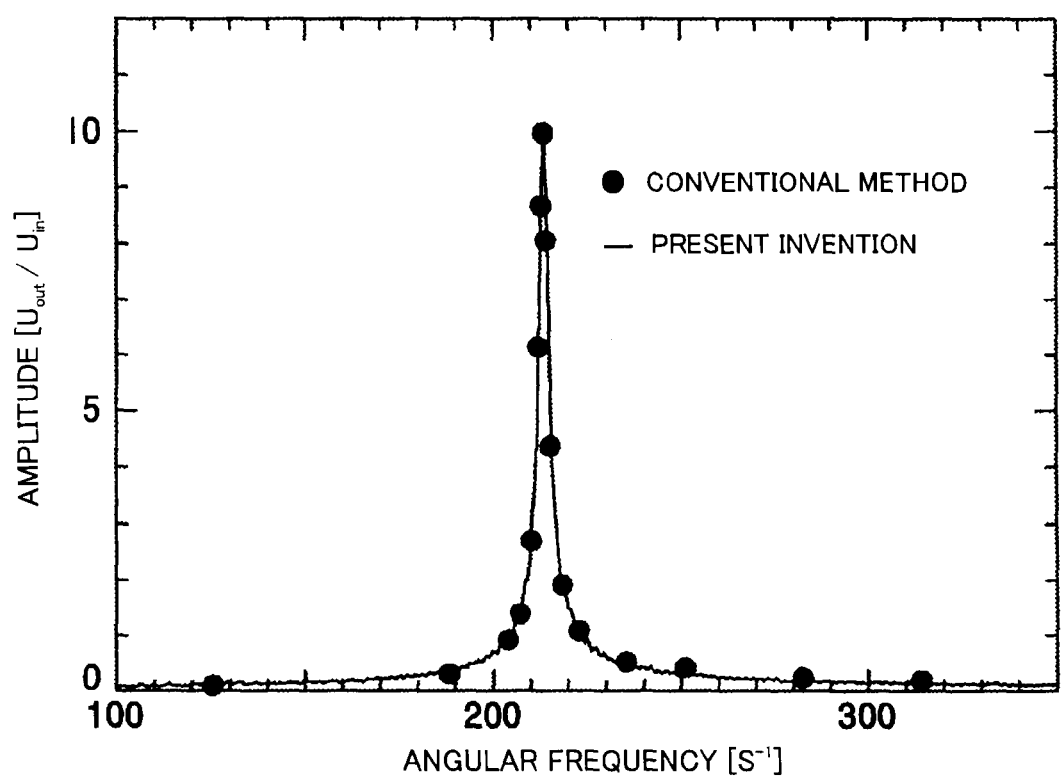
FIG. 6 shows a resonance shear curve obtained by applying Fourier transformation of the present invention to the damping oscillation as shown in FIG. 5 and a curve obtained by the conventional method.

FIG. 6 is a diagram showing the resonance shear curve obtained by applying Fourier transformation of the present invention to the damping oscillation shown in FIG. 5 and a curve obtained by the conventional method.

Here, the horizontal axis shows the oscillation frequency on the surface on one side of the sample, and the vertical axis shows an amplitude of the oscillation, which is shown by a ratio of the output voltage ($U_{out}$) measured by the capacitance type displacement gauge and the input voltage ($U_{in}$) applied to the piezoelectric element in the resonance shear measurement unit. The conventional method is a technique to measure point by point a response on the surface on one side of the sample to each oscillation frequency. FIG. 6 demonstrates that the present invention can measure the response on the surface on one side of the sample to the frequency quite well, and that the present invention is a method to measure continuously the response on the surface on one side of the sample for wide range of oscillation frequency in a short time.

In accordance with the present invention, by sandwiching a sample (solid, liquid, liquid crystal and the like) between two solid substrates, and by changing the thickness thereof, a change of the rheological properties of the sample, friction/lubrication properties, the interaction between the sample and the solid substrates, and the like can be measured. Furthermore, by using the substrate itself as a sample without any other sample sandwiched inbetween, mutual friction (lubrication) properties can be measured. Moreover, the surface may be modified by an adsorption method or a chemical modification method (LB (Langmuir-Brodgett) modification method). In addition, the frequency response of the sample can be measured not only by applying oscillation to the surface on one side of the sample in the horizontal direction but also by applying oscillation to the direction perpendicular to the surface.

In accordance with the present invention, it is not necessary to measure the shear response at each of the oscillation frequency point by point as in the conventional technology, and the measurement of the resonance shear curve can be performed, with ease, in short time, and with high precision.

In the following, a twin-path type shear stress measurement will be described as the other embodiment of the present invention.

Figure 7:
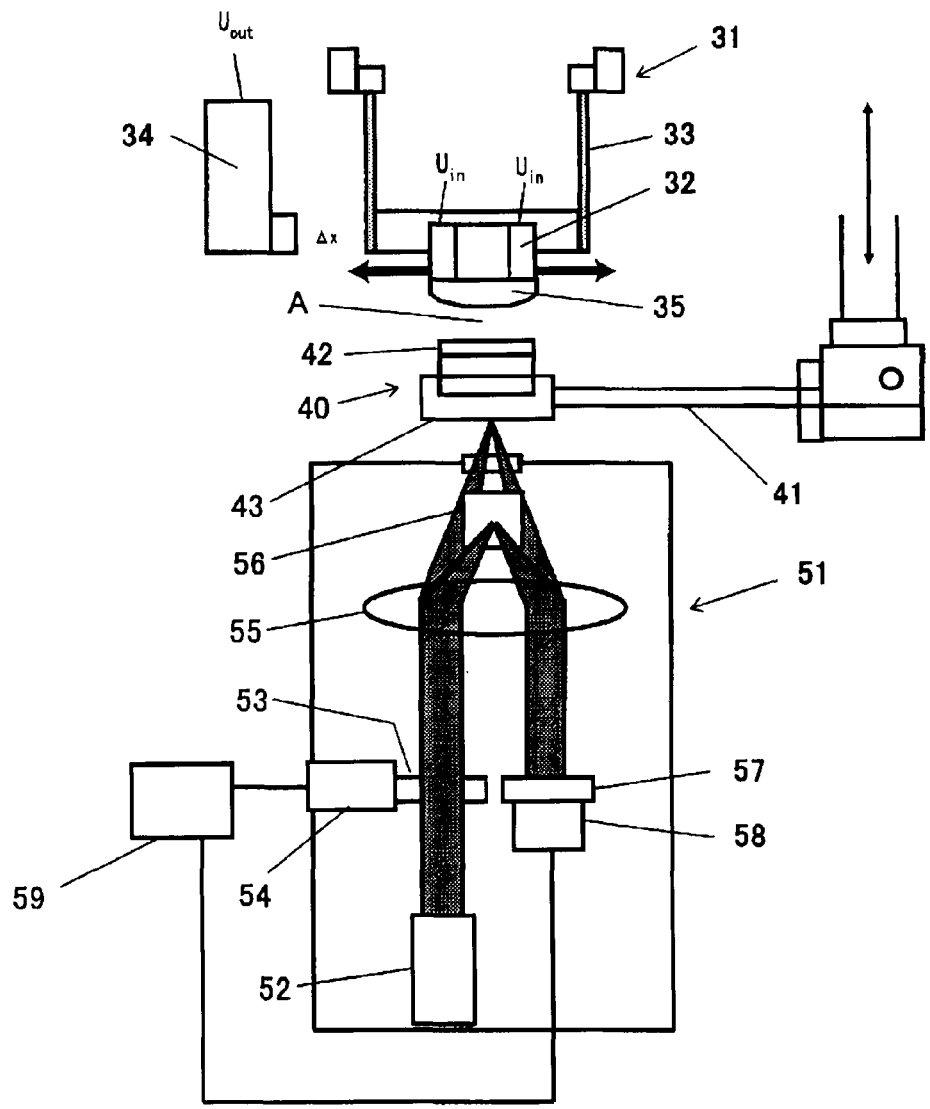
FIG. 7 is a schematic diagram of a twin-path type apparatus for sear stress measurement in accordance with the other embodiment of the present invention.

FIG. 7 is a schematic diagram showing a twin-path type apparatus for shear stress measurement in accordance with the other embodiment of the present invention.

In this figure, reference numeral 31 is a resonance shear measurement unit, 32 is a four-piece piezoelectric element to drive an upper surface horizontally, 33 is a leaf spring to support the four-piece piezoelectric element 32, 34 is a capacitance type displacement gauge (probe) to measure a horizontal displacement Δx of the leaf spring 33, 35 is an upper substrate which is fixed to the bottom of the four-piece piezoelectric element 32.

Also, an unit 40 to fix a bottom disk holder 42 holds the bottom disk holder 42 at a front edge of the leaf spring 41, and a mirror 43 is provided on a back side of the bottom disk holder 42. On the other hand, on the base part of the leaf spring 41, there is provided a driving apparatus (for example, a motor (not shown)) to drive the leaf spring 41 vertically.

Furthermore, 51 is a twin-path type measurement apparatus for a distance between surfaces, which comprises a laser light source 52, a diffraction grating 53 which receives the laser light from the laser light source 52 and divides it into a measuring light and a reference light, a piezoelectric element 54 to adjust the diffraction grating 53, a lens 55 to accept light from the diffraction grating 53, a fixed mirror 56 to receive the reference light which is a part of the laser light, a diffraction grating 57 which receives through the lens 55 the reference light reflected by the fixed mirror 56 and the measuring light reflected by the mirror 43 provided on a back side of the bottom disk holder, a photodiode 58 to receive the light passing through the diffraction grating 57, and a personal computer 59 connected to the piezoelectric element 54 and the photodiode 58.

By this configuration, a change of a distance between surfaces sandwiching the sample A can be measured by the twin-path type measurement apparatus for a distance between surfaces 51, whereas the upper surface of the sample A is attached to the resonance shear precise measurement unit 31 which measures the rheological property and the friction/lubrication property of the sample, thereby enabling measurement of the shear stress precisely.

Figure 8:
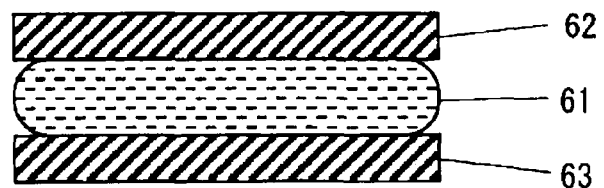
FIG. 8 is a schematic diagram of a sample used in an applicational example of a twin-path type apparatus for shear stress measurement in accordance with the other embodiment of the present invention.
Figure 9:
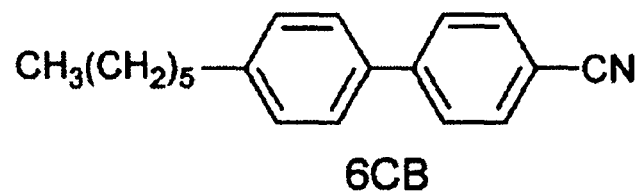
FIG. 9 shows a chemical formula of a liquid crystal (4-cyano-4-hexyl biphenyl, 6CB) as a sample sandwiched between surfaces of mica in accordance with the other embodiment of the present invention.
Figure 10:
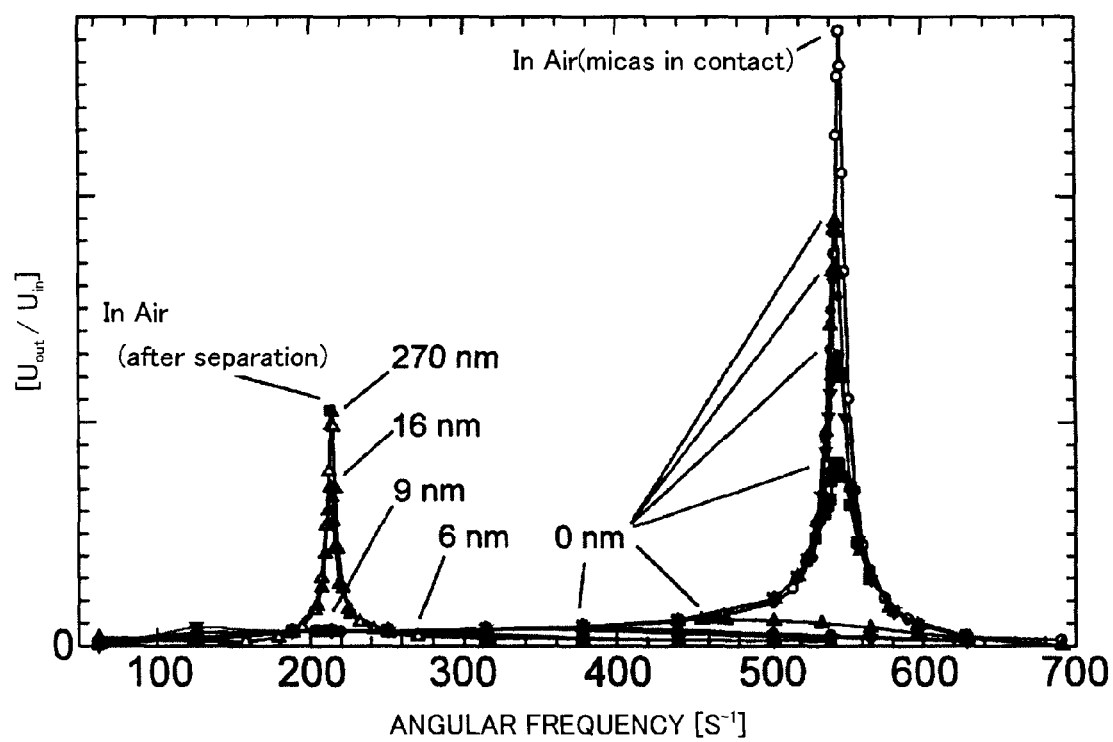
FIG. 10 shows a measurement result by the twin-path type apparatus for shear stress measurement of the present invention for a liquid crystal (4-cyano-4-hexyl biphenyl, 6CB) as a sample in accordance with another embodiment of the present invention.

FIG. 8 is a schematic diagram of a sample used in an applicational example of a twin-path type apparatus for shear stress measurement of the present invention, FIG. 9 shows a chemical formula of a liquid crystal (4-cyano-4-hexyl biphenyl, 6CB), and FIG. 10 shows the resonance curves measured by the twin-path type apparatus for shear stress measurement of the present invention for a liquid crystal (4-cyano-4-hexyl biphenyl, 6CB) as a sample.

As shown in FIG. 8, micas 62, 63 are disposed above and below the liquid crystal (4-cyano-4-hexylbiphenyl, 6CB) 61 which is a sample. That is, the liquid crystal 61 as a sample is disposed to be sandwiched between the mica 62 which is an upper substrate 35 and the mica 63 which is the bottom disk holder 42.

The chemical formula of a liquid crystal (4-cyano-4-hexyl biphenyl, 6CB) as a sample sandwiched between mica surfaces is shown in FIG. 9.

In the FIG. 10, the horizontal axis is an angular frequency ($s^{-1}$) on the upper surface of the sample, and the vertical axis is a ratio of the output voltage ($U_{out}$) measured by the capacitance type displacement gauge to the input voltage ($U_{in}$) applied to the piezoelectric element of the resonance shear precise measurement unit. In addition to the measurement result for the liquid crystal as a sample, a measurement result for the surfaces of the holding elements in a separated condition with no liquid crystal (sample) therebetween (in air (after separation)), and a measurement result for the surfaces of the holding elements in close contact with each other with no liquid crystal (sample) therebetween (in air (micas in contact)) are depicted for comparison. Solid lines shows resonance peaks for different distances of surfaces of the sample, the distances being shown on a side of each of the curves. Here, the distance between surfaces is defined to be 0 nm when no change of the distance between surfaces was observed when driving upward the bottom disk holder by a driving apparatus. By changing the distance between the surfaces, change of the resonance curve was observed. A plurality of peaks at 0 nm shows cases of a constant distance between the surfaces with different load.

Thus, the present invention enables measuring a change in rheological properties of the sample (liquid, solid, liquid crystal and the like), friction/lubrication properties, and a coupling intensity between the sample and the solid substrate while changing the thickness of the sample sandwiched between two solid substrates. Also by using the substrate itself as a sample, i.e., without any other sample sandwiched inbetween, mutual friction (lubrication) properties can be measured. Furthermore the surface may be modified by an adsorption or a chemical modification method (LB (Langmuir Blodgett) method)

Furthermore, the present invention does not need for a light to pass through the substrate and the sample because the reflection of a laser light is used, thereby enabling to measure the distance between surfaces and to measure the rheological property and the friction/lubrication property of the sample at different distances even if an opaque substrate and/or an opaque sample are used.

The present invention is not limited to the embodiments described above, but various modifications may be possible based on the essence of the present invention. These modifications are not excluded from the scope of the present invention.

INDUSTRIAL APPLICABILITIES

The resonance shear measuring method of the present invention as described in the first embodiment is suitable to measure simply, conveniently, and precisely properties of liquid thin films with thickness of a nanometer scale between solid surfaces.

The twin-path type apparatus for shear stress measurement of the present invention as described in the second embodiment can be used as a twin-path type apparatus for shear stress measurement which can measure shear stress precisely by using the twin-path method enabling to measure a distance between opaque substrates. Similarly to the resonance shear measuring method in the first embodiment, the apparatus in the second embodiment is also suitable to measure simply, conveniently, and precisely properties of liquid thin films with thickness of a nanometer scale between solid surfaces.

The invention claimed is:

1. A resonance shear measuring method to measure a shear response of a sample sandwiched between solid surfaces in a resonance shear measurement unit, along with a change in film thickness, the method comprising steps of:
    applying an input signal $U_{in}$ to a horizontal driving section of the resonance shear measurement unit,
    detecting an oscillation of a surface on one side of the sample sandwiched between the solid surfaces set in the resonance shear measurement unit by means of a displacement gauge, the output of detection being an output signal $U_{out}$, and,
    applying the output signal $U_{out}$ along with the input signal $U_{in}$ to a resonance shear signal analyzer,
        wherein a resonance shear curve is obtained by performing a Fourier transformation of a damping curve of the oscillation of the surface on one side of the sample.

2. A resonance shear measuring method to measure a shear response of a sample which is solid surfaces themselves without any other sample sandwiched between the solid surfaces in a resonance shear measurement unit, along with a change in film thickness, the method comprising steps of:
    applying an input signal $U_{in}$ to a horizontal driving section of the resonance shear measurement unit,
    detecting an oscillation of a surface on one side of the sample in the resonance shear measurement unit by means of a displacement gauge, the output of detection being an output signal $U_{out}$, and,
    applying the output signal $U_{out}$ along with the input signal $U_{in}$ to a resonance shear signal analyzer,
        wherein a resonance shear curve is obtained by performing a Fourier transformation of a damping curve of the oscillation of the surface on one side of the sample.

3. The resonance shear measuring method according to claim 1, wherein the sample is a thin film.

4. The resonance shear measuring method according to claim 1, wherein the sample is liquid.

5. The resonance shear measuring method according to claim 1, wherein the sample is a liquid crystal.

6. The resonance shear measuring method according to claim 1, wherein the sample has a thickness in nanometer size.

7. The resonance shear measuring method according to claim 1 or 2, wherein the sample has a surface modified by an adsorption or a chemical modification method.

8. The resonance shear measuring method according to claim 1 or 2, wherein the resonance shear curve is a frequency characteristics of shear response of the sample.

9. An apparatus for resonance shear measurement comprising:
    a waveform generator;
    a power source to which the waveform generator is connected;
    a resonance shear measurement unit to which the power source is connected and an input signal $U_{in}$ is applied;
    a displacement gauge to which the resonance shear measurement unit is connected;
    a resonance shear signal analyzer to which the displacement gauge and the power source are connected and to which an output signal $U_{out}$ along with an input signal $U_{in}$ are applied, the resonance shear signal analyzer comprising:
    (a) a timer section,
    (b) a Fourier transformation section to which the timer section and the displacement gauge are connected,
    (c) an amplitude spectrum generation section to which the Fourier transformation section is connected,
    (d) a normalization section of amplitude ($U_{out}/U_{in}$),
    (e) a resonance shear curve producing section; and
    a computer to which the waveform generator and the resonance shear signal analyzer are connected.

10. The resonance shear measuring method according to claim 1, wherein a shear stress measurement of the sample is performed by a combination of two methods: one method being a twin-path type measurement method for a distance between surfaces of the sample by irradiating a laser light to a mirror attached to a back side of a bottom disk holder and by detecting a phase change of the reflected light from the mirror, and the other method being the measurement method to measure rheological properties and friction/lubrication properties of the sample from a resonance curve.

11. The apparatus for resonance shear measurement according to claim 9 comprising:

(a) a precise shear device to give a horizontal displacement to a top disk holder,
(b) a displacement gauge to detect the horizontal displacement of the top disk holder,
(c) a fixing unit for fixing a lower surface of the sample, the unit comprising a leaf spring which holds at the front end a bottom disk holder, and a mirror disposed on a back side of a bottom disk holder,
(d) a driving apparatus to drive upward and downward the bottom disk holder by driving the fixing unit for fixing the lower surface of the sample,
(e) a twin-path type measurement unit for measuring a distance between surfaces, the unit irradiating a laser light to the mirror and measuring a distance between the upper surface of the sample and the lower surface of the sample based on a phase change of a reflected light from the mirror,
wherein rheological properties and friction/lubrication properties of the sample are measured per distance between the upper surface of the sample and the lower surface of the sample.

12. The apparatus for resonance shear measurement according to claim 11, wherein measurement on the rheological properties and friction/lubrication properties of the sample is performed based on a resonance curve of the sample.

13. The apparatus for resonance shear measurement according to claim 11 or 12, wherein the sample is a transparent sample or an opaque sample.

14. The apparatus for resonance shear measurement according to claim 11 or 12, wherein the sample is a liquid thin film.

15. The apparatus for resonance shear measurement according to claim 11 or 12, wherein the sample is a liquid crystal thin film.

16. The apparatus for resonance shear measurement according to claim 11 or 12, wherein the sample is an adsorption layer such as polymer and/or surfactant or a chemically modified film.

17. The apparatus for resonance shear measurement according to claim 11 or 12, wherein either one or both of the top disk holder and the bottom disk holder are opaque substrates.

* * * * *